United States Patent [19]

Snyder

[11] Patent Number: 5,379,758
[45] Date of Patent: Jan. 10, 1995

[54] HAND HELD SURGICAL RETRACTOR

[76] Inventor: Samuel J. Snyder, 57 Leach Ave., Park Ridge, N.J. 07656

[21] Appl. No.: 35,403

[22] Filed: Mar. 23, 1993

[51] Int. Cl.⁶ .......................... A61B 17/02; B25G 1/00
[52] U.S. Cl. .................... 128/20; 16/110 R; 15/143.1; 15/235.4
[58] Field of Search ................ 128/20, 17; 15/236.01, 15/235.4, 235.5, 143.1, 235.8, 144.1; 16/110 R, 113; 440/101; 135/71

[56] References Cited

U.S. PATENT DOCUMENTS

| | | | |
|---|---|---|---|
| 2,482,589 | 9/1949 | Maguire | 15/143.1 |
| 2,516,852 | 8/1950 | Burry et al. | 16/110 R |
| 2,608,192 | 8/1952 | Heitmeyer et al. | 128/20 |
| 3,196,865 | 7/1965 | Rose | 128/20 |
| 3,542,015 | 11/1970 | Steinman | 128/20 |
| 3,738,674 | 6/1973 | Pauls | 135/71 X |
| 3,998,217 | 12/1976 | Trumbull et al. | 128/20 |
| 4,116,232 | 9/1978 | Rabban | 128/20 |
| 4,248,256 | 2/1981 | Thomas | 135/71 X |
| 4,627,421 | 12/1986 | Symbas et al. | 128/20 |
| 4,836,190 | 6/1989 | Zwick | 128/20 |
| 4,888,846 | 12/1989 | Natale | 15/143.1 X |
| 4,934,352 | 6/1990 | Sullivan, Jr. | 128/20 |
| 4,962,561 | 10/1990 | Hamilton | 15/143.1 X |
| 5,000,163 | 3/1991 | Ray et al. | 128/20 |

FOREIGN PATENT DOCUMENTS

| | | | |
|---|---|---|---|
| 2744509 | 5/1978 | Germany | 128/897 |
| 2248034 | 3/1992 | United Kingdom | 16/113 |

OTHER PUBLICATIONS

Traux-Greene-"Gynecological Instruments", p. 1477--date unknown.

*Primary Examiner*—Stephen R. Chow
*Assistant Examiner*—Donna L. Maraglio
*Attorney, Agent, or Firm*—Anthony F. Cuoco

[57] ABSTRACT

A retractor has a blade which is in contact with a surgical wound. A handle has one end supported by the blade and extends substantially normal thereto, and has an opposite free end. A brace plate is attached to the free end of the handle and fits against the user's forearm to stabilize the retractor. A hand grip is attached to the handle between the blade and the brace plate. The arrangement is such that a fulcrum is created at the attachment between the hand grip and the handle, whereby the larger and stronger muscles of the user are available with a mechanical advantage to control the retractor. The blade may assume a variety of configurations and the blade, hand grip and brace plate are pivotable in a variety of planes relative to the plane of the handle.

17 Claims, 4 Drawing Sheets

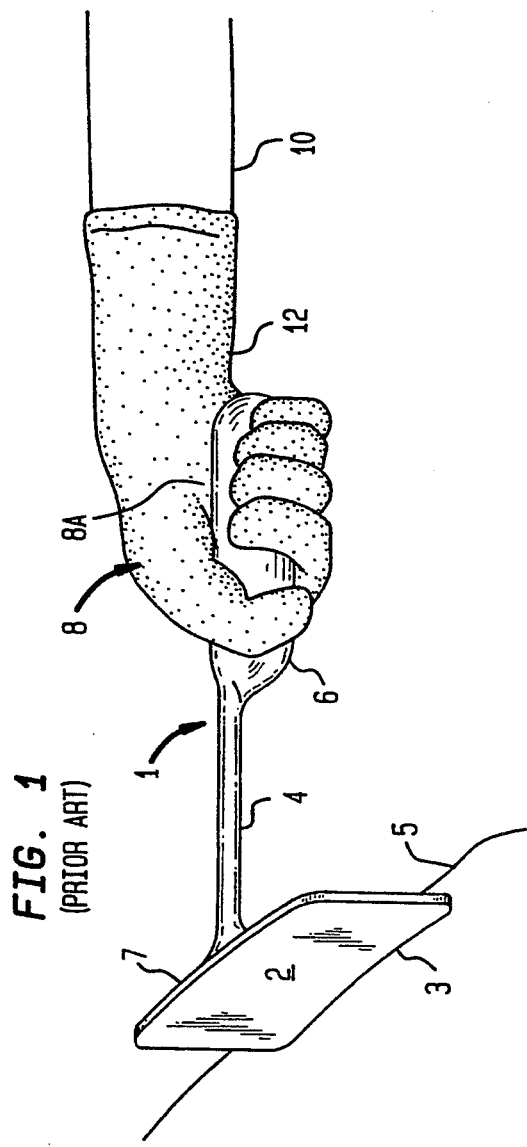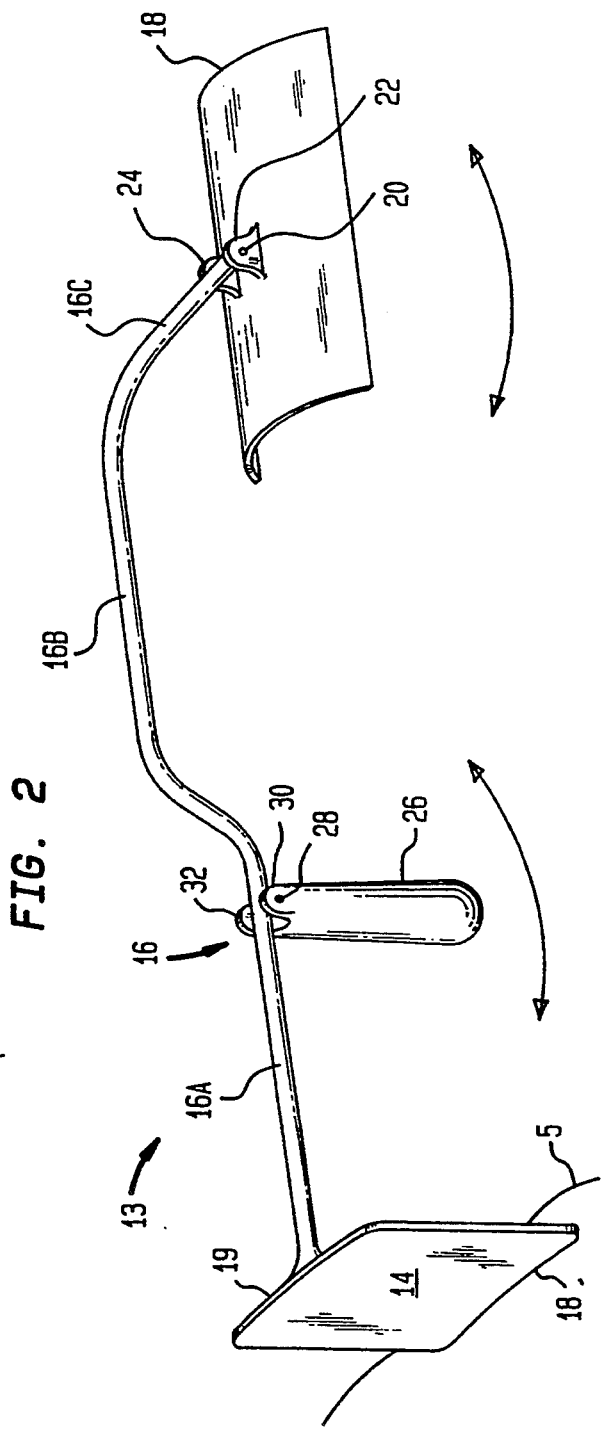

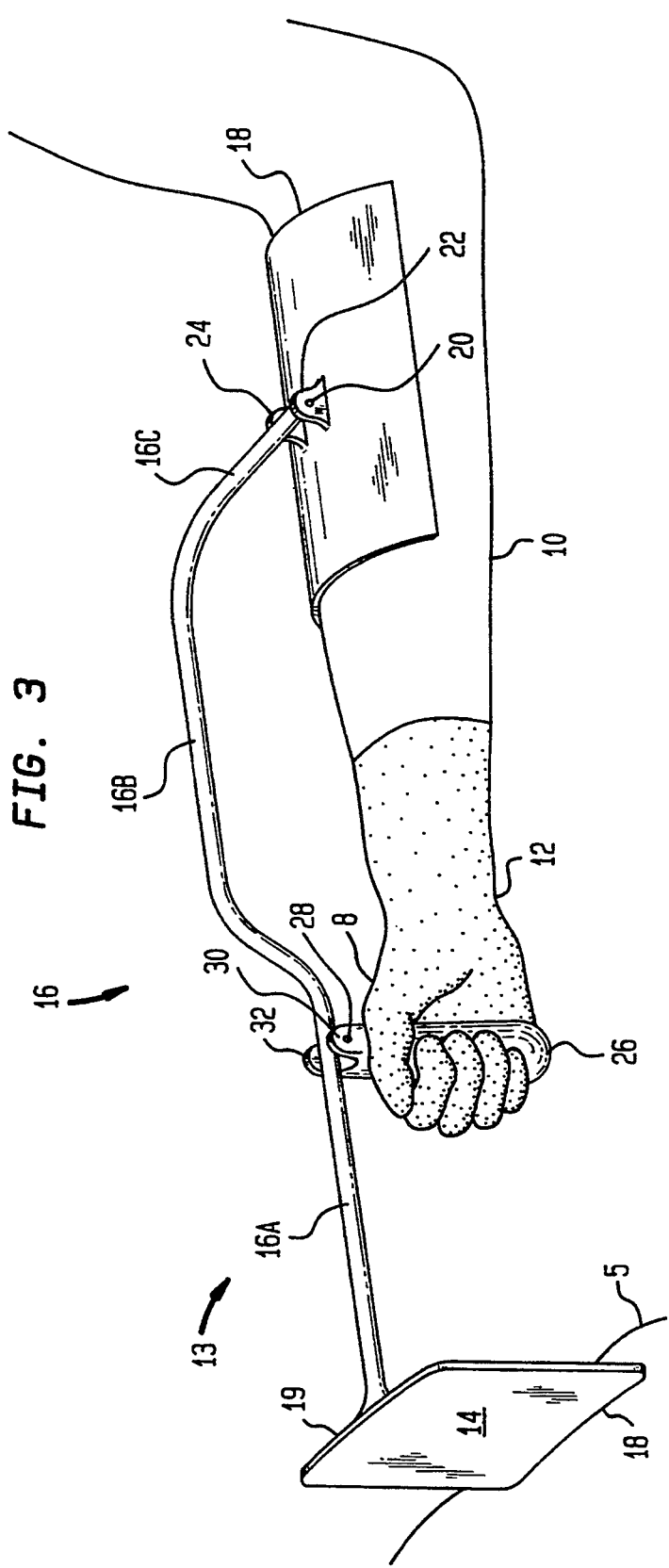

HAND HELD SURGICAL RETRACTOR

BACKGROUND OF THE INVENTION

This invention relates generally to surgical retractors for exposing an operative field during a surgical procedure and, more particularly, to a hand held surgical retractor for the purpose described which minimizes fatigue and discomfort of a surgeon-user who must apply maximum force to the retractor for even very short periods of time.

Uncompromised exposure of an operative field is required for successful surgical procedures. This exposure is achieved by retracting tissues, organs, muscles or bones, as the case may be, away from the operative field. Most surgical procedures are performed by a team including an operative surgeon and at least one assistant surgeon, as required by the complexity of the procedure. The operative surgeon selects and positions the retractor but it is the responsibility of the assistant surgeon to control the retractor once it is set in place.

Prior art hand held surgical retractors have a blade which is maintained in contact with a surgical wound and a handle which is manipulated by the assistant surgeon as may be necessary to maintain exposure of the operative field during the course of the surgical procedure.

The handle is grasped by the assistant surgeon while his/her wrist and hand manipulate the retractor. The forearm muscles provide the required retracting force. It will be readily appreciated that fatigue of the hand, wrist and forearm is a common problem, particularly when the retractor must be controlled for long periods of time as in a complicated surgical procedure. In this regard, it will be appreciated that many surgical procedures extend over a period of several hours. The assistant surgeon may often have a retractor in each hand and may be required to control the retractors with an uninterrupted constant force for these several hours.

The control of prior art hand held retractors originates at the palm of the hand. The wrist joint is used for positioning, stabilizing and applying the retracting force. This rapidly results in hand and forearm fatigue. The force applied to the retractor is exerted by the small muscles of the forearm. The stronger muscles of the arm, shoulder and chest are not active when using a palm based, hand held retractor.

Prior art hand held surgical retractors also require the hand to be maintained at a maximum oblique orientation so that the retractor is positioned parallel to the forearm. The oblique orientation occurs from deviation of the hand at the wrist. This prolonged, unnatural position of the hand further contributes to fatigue and discomfort due to holding a prior art retractor for extended periods of time, or when maximal muscle forces are required.

The present invention obviates the aforementioned disadvantages of prior art hand held surgical retractors by separating and distributing the elements of retractor control to individual regions of the upper extremity of the surgeon controlling the retractor. This prevents the aforementioned fatigue irrespective of when, where or for how long the retractor is used. It should be noted that with prior art retractors, when maximal isometric force is required for retraction of a surgical wound, intolerable fatigue can develop in as short a period of five minutes. With the retractor of the present invention, this fatigue is almost completely eliminated and the surgeon-user can apply the required force for an almost indefinite period. Further, the ergonomic design of the retractor of the present invention eliminates the aforementioned oblique orientation of the hand at the wrist so as to be advantageous over prior art retractors of the type described.

SUMMARY OF THE INVENTION

This invention contemplates a hand held surgical retractor including a blade having one edge for contacting a surgical wound and a handle supported at one end thereof by an opposite edge of the blade and extending substantially normal thereto so as to have a free end. A brace plate is pivotally attached to the free end of the handle and stabilizes the retractor against a user's forearm. A hand grip is pivotally attached to the handle and extends away therefrom toward the one blade edge.

Variations in the configuration described are contemplated by the invention. For example, the blade can be in a variety of forms as may suit the needs of the operative surgeon or the anatomical region in which the retractor is being used. The blade may be telescopically supported by the handle so that the distance that the blade extends from said handle is adjustable, as may be desired. Further, the blade may be displaceable relative to the handle in one or another direction, or may De universally displaceable, as the case may be.

BRIEF DESCRIPTION OF THE DRAWINGS

FIG. 1 is an isometric representation illustrating a typical prior art hand held surgical retractor as grasped by a user.

FIG. 2 is an isometric representation illustrating a hand held surgical retractor in accordance with the invention.

FIG. 3 is an isometric representation illustrating the hand held surgical retractor of the invention illustrated in FIG. 2 as grasped by a user.

DETAILED DESCRIPTION OF THE INVENTION

Figure 4:
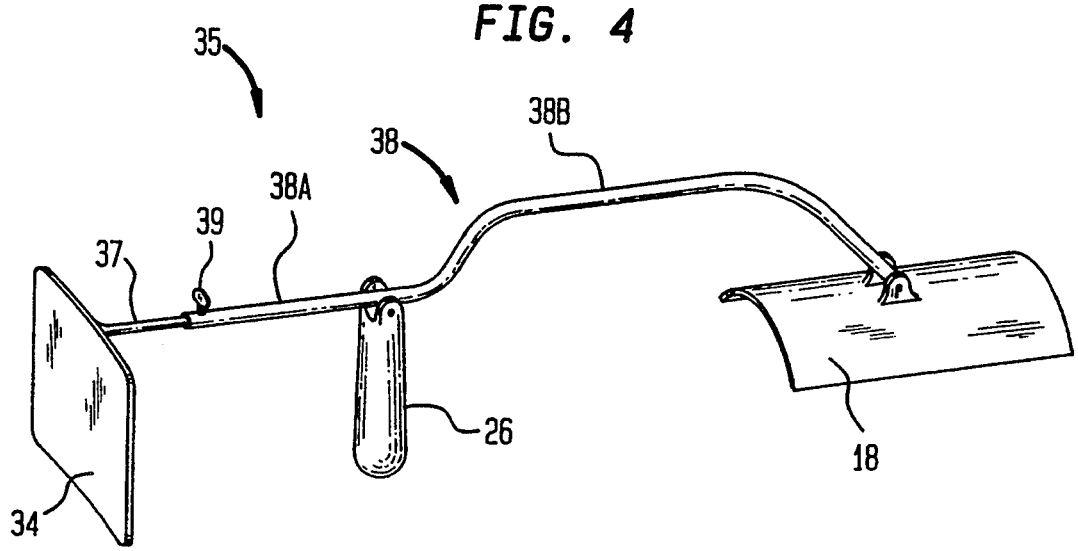
FIG. 4 is an isometric representation illustrating a form of the invention wherein the blade of the hand held surgical retractor of the invention is telescopically arranged with the handle thereof.

With reference first to FIG. 1, a prior art hand held surgical retractor is designated generally by the numeral 1 and includes a blade 2. Blade 2 has an edge 3 which is in contact with a surgical wound 5 and an opposite edge 7. A handle 4 is integral with edge 7 of blade 2 so as to be supported thereby at approximately the center thereof and extends away therefrom in a plane substantially normal to the plane of the blade. Handle 4 has a free end which carries a hand grip 6. Hand grip 6 is grasped by a surgeon-user in the palm 8A of the user's hand 8.

It will be appreciated that a retracting force is applied by the user primarily by the muscles in the user's forearm 10. The wrist 12 and hand 8 of the user are used to manipulate retractor 1.

As will be evident from FIG. 1, retractor 1, grasped by the user as aforenoted, requires the hand to maintain an oblique orientation so that handle 4 is substantially parallel to forearm 10. The oblique orientation occurs due to the twisting of hand 8 at wrist 12 and is, as will be readily discerned, an unnatural position of the hand. This unnatural position, when prolonged as may well be the case, contributes to fatigue and discomfort of the user.

With reference now to FIGS. 2 and 3, the hand held retractor of the invention is designated generally by the numeral 13 and includes a blade 14 and a handle 16. Blade 14 has an edge 17 which is in contact with surgical wound 5 and an opposite edge 19. Handle 16 has a linear section 16A which is integral at one end thereof with blade edge 19 so as to be supported thereby at substantially the center thereof and extends away therefrom so as to merge at approximately the center of handle 16 with a generally arcuate handle section 16B. The axis of handle section 16B is offset from the axis of handle section 16A in a direction away from blade edge 19 and section 16B has a free end 16C. Handle sections 16A and 16B are coplanar, with the plane of the sections being substantially normal to the plane of blade 14.

Free end 16C of handle section 16B pivotally supports a generally convex arcuate brace plate 18 via a pivot pin 20 which extends through an ear 22 of the brace plate, through free end 16C and through an ear 24 of brace plate 18. Ear 24 is in parallel spaced relation with ear 22. The arrangement is such that brace plate 18 is pivotable about the axis of pivot pin 20 i.e., an axis substantially normal to the plane of handle 16 as shown by the arrow in FIG. 2.

At approximately the point where handle sections 16A and 16B merge, a hand grip 26 is pivotally attached to handle 16 via a pivot pin 28 which extends through an ear 30 on the handle, through handle 16 and through an ear 32 on the handle, with ears 30 and 32 being in parallel spaced relation. The arrangement is such that hand grip 26 is pivotable about an axis substantially normal to the plane of handle 16 as shown by the arrow in FIG. 2.

Brace plate 18 as shown stabilizes the retractor against forearm 10 of the user as will now be discerned from FIG. 3.

It will be appreciated that a fundamental disadvantage of the prior art retractor as shown in FIG. 1 is the considerable lack of leverage available to the user. The present invention as shown in FIGS. 2 and 3 overcomes this disadvantage by creating a fulcrum at the pivotal connection between hand grip 26 and handle 16. Thus, in the prior art retractor, the muscles of the arm function directly to control the retractor. The retractor of the present invention not only enlists larger and stronger muscles of the user for the purpose intended, but achieves a mechanical advantage not heretofore available.

In using the present invention, it will be realized, as shown in FIG. 3, that retractor 13 is grasped at hand grip 26 with the wrist and hand of the user in neutral alignment. Blade 14 is positioned in surgical wound 5. A retracting force is applied to the wound which is transmitted to brace plate 18 positioned against the user's forearm 10.

Hand 8 is maintained in the neutral position and thus energy is conserved and the retractor can be controlled with minimum fatigue. Excellent stabilization of the retractor is achieved by the aforenoted bracing of the retractor against forearm 10 via brace plate 18. Thus, in effect, a static stabilization is provided by the transfer of force through the retractor to the radius bone of the user's forearm. The force to control the retractor is supplied by the muscles of the arm, shoulder and chest wall of the user. In this connection it is noted that the force required to control the retractor is shifted from the weaker forearm muscles to the substantially stronger arm, shoulder and chest wall muscles, as is desireable to decrease fatigue and increase endurance of the user.

Variations in the configuration of the disclosed retractor are within the contemplation of the invention and are described with reference to FIGS. 4–11. Thus, FIGS. 5–8 show variations in the retractor blade configuration as will next be described.

Figure 5:
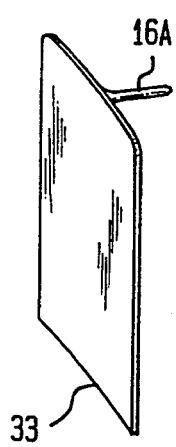
FIGS. 5, 6, 7 and 8 are isometric representations illustrating different blade forms of the hand held surgical retractor of the invention.
Figure 6:
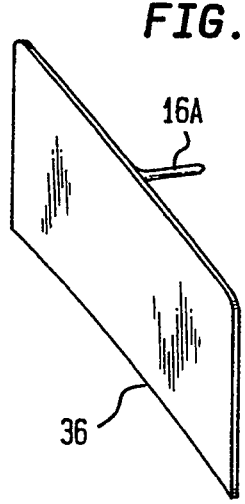
Figure 7:
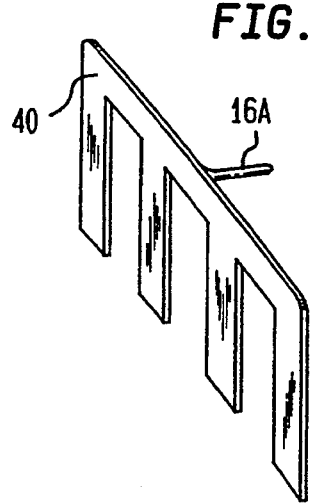
Figure 8:
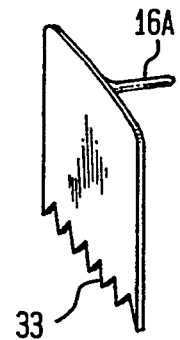

FIG. 5 shows a retractor blade 33 which is narrow and long and FIG. 6 shows a retractor blade 36 which is shallow and wide. FIG. 7 shows a retractor blade 40 which has a rake-like configuration and FIG. 8 shows a retractor blade 42 which has teeth or serrations at the bottom edge thereof. Each of the forms of the retractor blades shown in FIGS. 5–8 can be used in the form of the invention illustrated in FIGS. 2 and 3 and in accordance with the needs of the utilizing surgeon or the anatomical region in which the retractor is intended to function.

A particular form of the hand held retractor of the invention is shown in FIG. 4 and is designated generally by the numeral 35, wherein the retractor handle is in a telescoping configuration.

Thus, a blade 34 which is similar to blade 14 shown in FIGS. 2 and 3 has a stem 37 integral therewith and extending therefrom in a manner similar to that described in regard to handle section 16A also shown in FIGS. 2 and 3. A handle 38 has sections 38A and 38B which generally correspond to handle sections 16A and 16B, respectively, likewise shown in FIGS. 2 and 3. In the form of the invention shown in FIG. 4, however, handle section 38A is hollow so as to telescopically receive stem 37. The stem is locked in a desired telescoped position by a screw or the like 39.

It will be appreciated that in all other respects, retractor 35 shown in FIG. 4 is like retractor 13 shown in FIGS. 2 and 3. Further, blade 34 may be interchangeable with blades 33–42, as shown in FIGS. 5–8 when the blades have stems such as 37 extending therefrom instead of handle section 16A, as is contemplated by the invention.

Figure 9:
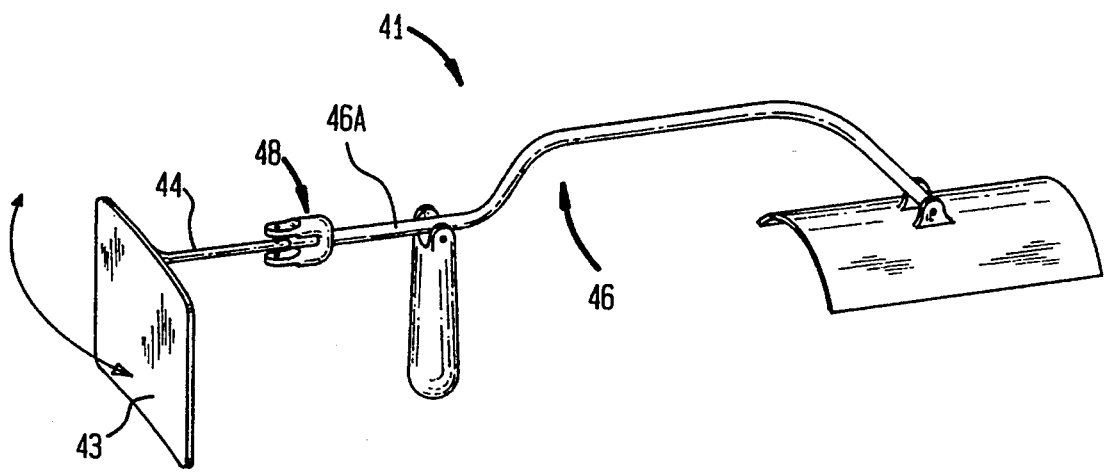
FIG. 9 is an isometric representation illustrating a hand held surgical retractor according to the invention, wherein the blade is displaceable in one direction as contemplated by the invention.
Figure 10:
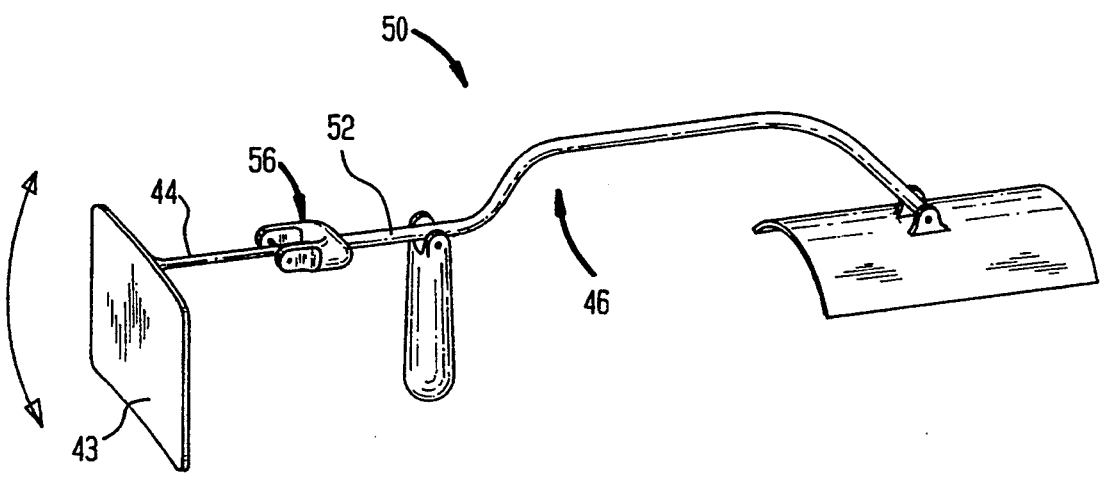
FIG. 10 is an isometric representation illustrating a hand held surgical retractor according to the invention wherein the blade is displaceable in another direction as contemplated by the invention.
Figure 11:
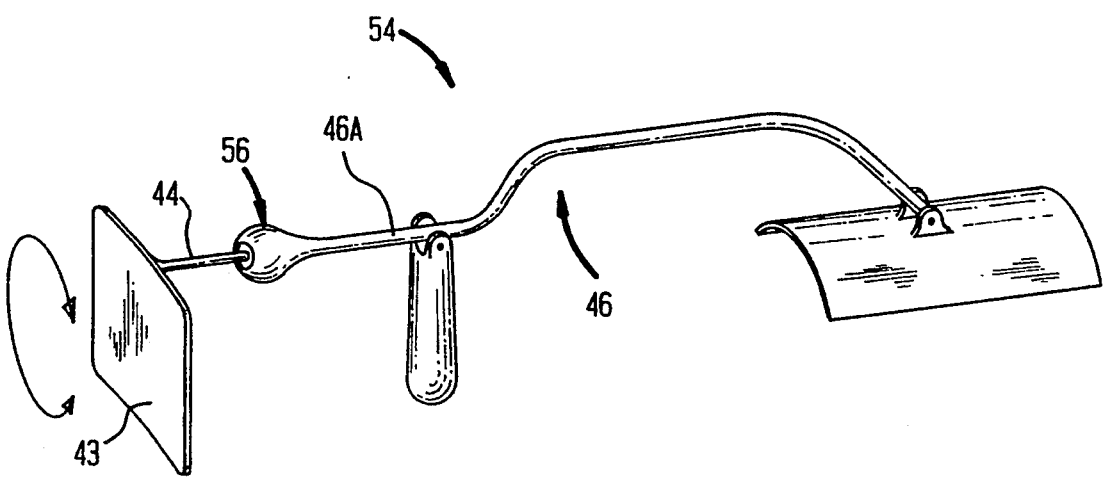
FIG. 11 is an isometric representation illustrating a hand held surgical retractor according to the invention wherein the blade is universally displaceable as contemplated by the invention.

Still other forms of the invention are shown in FIGS. 9–11. Thus, in FIG. 9, a retractor 41 has a blade 43 which is similar to blade 34 (FIG. 4). However, instead of having a stem such as 37 integral with and extending therefrom, blade 43 has a link 44 integral therewith and extending therefrom. A handle 46 has a section 46A. Link 44 and handle section 46A are coupled by a pivot joint 48, whereby blade 43 is pivotable about an axis parallel to the plane of handle section 46A as shown by the arrow.

With reference to FIG. 10, a retractor 50 is similar to retractor 40, except that link 44 is coupled to handle section 46A by a pivot joint 52, whereby plate 43 is pivotable about an axis normal to the plane of handle section 46A as shown by the arrow.

Likewise, and with reference to FIG. 11, a retractor 54 is similar to retractors 41 and 50, except that link 44 is coupled to handle section 46A by a ball joint 56, whereby blade 43 is universally pivotable relative to handle section 46A as shown by the arrow.

In this regard, it will be understood that while brace plate 18 and hand grip 28 are earlier shown and described as being pivotable about axes normal to the plane of handle 16, it will be understood that the invention contemplates as well that the brace plate and hand grip are pivotable about axes parallel to the plane of the retractor handle and, indeed, are universally pivotable via pivot joints such as described above with reference to FIGS. 9 and 11.

It will be appreciated that blade 43 may assume the configuration of blades 33-42 shown in FIGS. 5-8, respectively.

There has thus been described a hand held surgical retractor which is grasped with the wrist and hand of the user being maintained in neutral alignment, thereby avoiding prolonged, unnatural, oblique orientation of the user's hand at the wrist.

The muscles of the user's forearm are only used to grasp the handle of the retractor, but are not used to stabilize, position and exert force on said retractor. Fatigue at the wrist and forearm muscles is therefore significantly reduced since stabilizing and retracting forces are achieved via the muscles of the upper extremities of the user's body.

Stabilization of the retractor is achieved by bracing the retractor against the forearm. This is contrary to stabilization as required in prior art hand held retractors, wherein the stabilization requires muscle forces which result in muscle fatigue. The stabilization is thus achieved with a minimal exertion of energy. The stabilization via the forearm as aforenoted significantly increases the leverage of the retractor when compared with prior art hand held retractors.

In effect, then, the hand held retractor of the invention makes use of the stronger muscles of the user's arm, shoulder and chest to provide the retracting force, thereby being an ergonomic improvement over prior art hand held retractors.

The basic form of the retractor of the invention is illustrated with reference to FIGS. 2 and 3, with variations therein being illustrated with reference to FIGS. 4-11. The variations preserve the improved ergonomics, improved leverage and advantages of reduced muscle fatigue and increased user endurance, as does the basic configuration of the invention.

With the above description of the invention in mind, reference is made to the claims appended hereto for a definition of the scope of the invention.

What is claimed is:

1. A hand held surgical retractor, comprising:
   a blade having one edge for contacting a surgical wound and an opposite edge, said blade lying substantially in a first plane;
   a handle having one end supported by the opposite edge the blade, said one end extending along a first longitudinal axis, said axis extending substantially normal to said first plane, said handle further having an opposite free end;
   a brace plate arranged to fit against a forearm of a used and pivotally attached to the opposite free handle end; and
   a grip for being gripped by the hang of the user, sale grip being pivotally attached to the handle between the blade and brace plate.

2. A hand held surgical retractor as described by claim 1, including:
   the blade having a stem supported by the opposite edge of the blade and extending outwardly therefrom along said first longitudinal axis;
   the one handle end being arranged to telescopically receive the stem therewithin; and
   means for securing the stem in a desired telescoped position within the one handle end, whereby the one handle end is supported by the opposite edge of the blade.

3. A hand held surgical retractor as described by claim 1, including:
   the blade having a link supported by the opposite edge of the blade and extending outwardly therefrom along said first longitudinal axis;
   a pivot joint for coupling the link to the one handle end, whereby the one handle end is supported by the opposite edge of the blade.

4. A hand held surgical retractor as described by claim 3, wherein:
   the pivot joint is arranged so that the blade and the link extending from the opposite edge of the blade are pivotable about an axis substantially parallel to the plane of the handle.

5. A hand held surgical retractor as described by claim 3, wherein:
   the pivot joint is arranged so that the blade and the link extending from the opposite edge of the blade are pivotable about an axis substantially normal to the plane of the handle.

6. A hand held surgical retractor as described by claim 3, wherein:
   the pivot joint is arranged so that the blade and the link extending from the opposite edge of the blade are universally pivotable relative to the handle.

7. A hand held surgical retractor as described by claim 1, wherein:
   the width of the blade is substantially longer than its length.

8. A hand held surgical retractor as described by claim 1, wherein: the length of the blade is substantially longer than its width.

9. A hand held surgical retractor as described by claim 1, wherein:
   the blade has a rake-like configuration.

10. A hand held surgical retractor as described by claim 1, wherein:
    the one edge of the blade has serrations thereon.

11. A hand held surgical retractor as described by claim 1, wherein the handle includes:
    a first generally linear section extending along said first longitudinal axis from the one handle end to approximately the center of the handle;
    a second generally arcuate section merging with the linear section at approximately the center of the handle and extending along a second longitudinal axis to the opposite free handle end; and
    the axis of the second section being offset from the axis of the first section away from the opposite blade edge.

12. A hand held surgical retractor as described by claim 1, wherein:
the brace plate is pivotally attached to the free handle end so as to be universally pivotable.

13. A hand held surgical retractor as described by claim 1, wherein:
the brace plate is pivotally attached to the free handle end so as to be pivotable about an axis substantially parallel to the plane of the handle.

14. A hand held surgical retractor as described by claim 1, wherein:
the brace plate is pivotally attached to the free handle end so as to be pivotable about an axis substantially normal to the plane of the handle.

15. A hand held surgical retractor as described by claim 1, wherein:
the hand grip is pivotally attached to the handle between the blade and the brace plate so as to be pivotable about an axis substantially normal to the plane of the handle.

16. A hand held surgical retractor as described by claim 1, wherein:
the hand grip is pivotally attached to the handle between the blade and the brace plate so as to be pivotable about an axis substantially parallel to the plane of the handle.

17. A hand held surgical retractor as described by claim 1, wherein:
the hand grip is pivotally attached to the handle between the blade and the brace plate so as to be universally pivotable.

* * * * *